US005618953A

United States Patent [19]

Abe et al.

[11] Patent Number: 5,618,953

[45] Date of Patent: Apr. 8, 1997

[54] PROCESS FOR PRODUCING 3-METHYLTETRAHYDROFURAN

[75] Inventors: Takafumi Abe; Fumio Tanaka; Hiroyuki Nitobe; Masaki Takemoto, all of Niigata, Japan

[73] Assignee: Mitsubishi Gas Chemical Co., Inc., Tokyo, Japan

[21] Appl. No.: 595,271

[22] Filed: Feb. 1, 1996

[30] Foreign Application Priority Data

| | | | |
|---|---|---|---|
| Feb. 10, 1995 | [JP] | Japan | 7-022806 |
| Feb. 10, 1995 | [JP] | Japan | 7-022807 |
| Apr. 25, 1995 | [JP] | Japan | 7-101106 |

[51] Int. Cl.[6] .......... C07D 307/02

[52] U.S. Cl. .......... 549/508

[58] Field of Search .......... 549/508

[56] References Cited

U.S. PATENT DOCUMENTS

| | | | |
|---|---|---|---|
| 3,859,369 | 1/1975 | Copelin | 260/635 R |
| 4,124,600 | 11/1978 | Jenkins, Jr. | 549/508 |
| 4,772,729 | 9/1988 | Rao | 549/508 |

FOREIGN PATENT DOCUMENTS

| | | |
|---|---|---|
| 0133739 | 3/1985 | European Pat. Off. . |
| 0340970 | 11/1989 | European Pat. Off. . |
| 0589314 | 3/1994 | European Pat. Off. . |
| 0657384 | 6/1995 | European Pat. Off. . |
| 3801863 | 8/1988 | Germany . |
| 63-185937 | 8/1988 | Japan . |

OTHER PUBLICATIONS

Elisabeth Dane et al, "Uber die Umsetzung von Brenz--traubensäure mit primaren aromatischen Aminen zu Derivaten der Brenzweinsäure und der Acetursäure Reaktionen der Brenztraubensäure I", Justus Liebigs Annalen der Chemie, vol. 607, 1957, pp. 92–108.

Database WPI, Section Ch, Week 9549, Derwent Publications Ltd., London, GB, AN 95–380015 of JP–A–07 258 149 (Kuraray Co., Ltd.) Oct. 9, 1995.

*Primary Examiner*—Amelia Owens

*Attorney, Agent, or Firm*—Frishauf, Holtz, Goodman, Langer & Chick, P.C.

[57] ABSTRACT

A process for producing 3-methyltetrahydrofuran, wherein in a first step, prussic acid is reacted with methyl methacrylate to produce methyl 3-cyanoisobutyrate. The methyl 3-cyanoisobutyrate is then reacted with water and sulfuric acid to produce a resultant product which is reacted with a $C_1$–$C_8$ aliphatic alcohol to produce a methylsuccinic acid ester. The methylsuccinic acid ester is catalytically hydrogenated to prepare the 3-methyltetrahydrofuran. Alternatively, the methyl 3-cyanoisobutyrate is hydrated to produce methyl 3-carbamoylisobutyrate, which is then reacted with a formic acid ester to form a methylsuccinic acid ester and formamide and the resultant methylsuccinic acid ester is catalytically hydrogenated. The 3-methyltetrahydrofuran is produced in high selectivity and in a commercially advantageous manner from inexpensive reactants. The 3-methyltetrahydrofuran is useful as a commoner for producing polyether glycol, which is utilized as starting raw material for preparing spandex fiber.

15 Claims, No Drawings

PROCESS FOR PRODUCING 3-METHYLTETRAHYDROFURAN

BACKGROUND OF THE INVENTION

1. Field of the Invention

The present invention relates to a novel process for producing 3-methyltetrahydrofuran. More particularly, it pertains to a process for producing, in an efficient and industrially advantageous manner, 3-methyltetrahydrofuran which is useful, for example, as a comonomer for polyether glycol to be used as a starting raw material for spandex fibers, by the use of inexpensive starting raw materials.

2. Description of Related Arts

It is known that 3-methyltetrahydrofuran is a useful compound, for example, as a comonomer for polyether glycol which is a starting raw material for spandex fibers. The 3-methyltetrahydrofuran can be produced by any of a variety of conventional processes, which however, can not necessarily be said to be a satisfactory process because of expensiveness in starting raw materials, low selectivity to the objective product, severe conditions in the reaction or the like.

According to Japanese Patent Application Laid-Open No. 218669/1988, 3-methyltetrahydrofuran is produced together with 3- and 4-methylbutyrolactone by the hydrogenation of citric acid, but the selectivity to the objective product is about 70%. According to U.S. Pat. No. 3956318, 3-methyltetrahydrofuran is produced by the catalytic hydrogenation of an epoxide in liquid phase in the presence of a protonic acid, but the epoxide as a starting raw material is expensive. According to Japanese Patent Application Laid-Open No. 62835/1990, 3-methyltetrahydrofuran is produced by the cyclization of a diol which is obtained by the catalytic hydrogenation of 4-hydroxybutyraldehyde or 2-hydroxytetrahydrofuran in the presence of an aldehyde, but the diol as a starting raw material is expensive and besides, the objective product is accompanied by the by-production of tetrahydrofuran. In addition, there is disclosed a process for producing 3-methyltetrahydrofuran by the hydrogenation of methylmaleic acid or methylsuccinic acid in Japanese Patent Publication No. 9463/1974, but the process is evidently difficult to put into industrial practice, since the starting raw material is difficult to procure and besides the hydrogenation is carried out under severe conditions.

According to Japanese Patent Application Laid-Open No. 22405/1973, 3-methyltetrahydrofuran is produced by a process comprising the steps of hydroformylating 1,4-butenediol in the presence of a catalyst; separating the catalyst from the reactant; then catalytically hydrogenating the aqueous solution of the hydroformylated product which is presumed to be 2-formyl-1,4-butanediol to obtain 2-methyl-1,4-butanediol; and cyclizing the resulting 2-methyl-1,4-butanediol to obtain 3-methyltetrahydrofuran. According to Japanese Patent Laid-Open No. 117258/1993 and Japanese Patent Application Publication No. 55179/1992, 3-methyltetrahydrofuran is produced by the cyclization of diol which is obtained by the catalytic hydrogenation of 1,4-butynediol or 1,4-butenediol in the presence of an aldehyde. However, the 1,4-butynediol and 1,4-butenediol as the starting raw material in the above process are both expensive, since they are obtained from acetylene and besides, the objective product is accompanied with the by-production of tetrahydrofuran.

According to Japanese Patent Application Laid-Open No. 219981/1994, 3-methyltetrahydrofuran is produced together with 2-methyl-1,4-butanediol by the catalytic hydrogenation of itaconic acid, 3-formyl-2-methylpropionic acid or an ester thereof, but the starting raw material composed of itaconic acid or 3-formyl-2-methylpropionic acid is expensive. In view of the above, the conventional processes as mentioned above are far from satisfactory from the industrial point of view because of expensiveness in starting raw material, low selectivity to the objective 3-methyltetrahydrofuran or the like.

SUMMARY OF THE INVENTION

It is an object of the present invention to provide a process for producing 3-methyltetrahydrofuran in high selectivity and in an industrially advantageous manner by the use of inexpensive starting raw materials, while overcoming the disadvantages involved in the conventional processes for producing 3-methyltetrahydrofuran.

Under such circumstances, intensive research and investigation were accumulated by the present inventors in order to attain the above-mentioned object. As a result, it has been found that the above-mentioned object can be attained by a process in which at first methyl 3-cyanoisobutyrate is produced from prussic acid and methyl methacrylate and then is reacted with water and sulfuric acid, the resulting reaction product is reacted with an alcohol to form a methylsuccinic acid ester, and subsequently the resultant ester is catalytically hydrogenated. It has also been found that the object can be attained by a process in which the aforesaid methyl 3-cyanoisobutyrate is hydrated to form methyl 3-carbamoylisobutyrate, which is then reacted with a formic acid ester to form a methylsuccinic acid ester and formamide, and subsequently the resultant methylsuccinic acid ester is catalytically hydrogenated. The present invention has been accomplished by the above-mentioned finding and information.

That is to say, the present invention provides, as the first aspect thereof, a process for producing 3-methyltetrahydrofuran which comprises the first step of (a) producing methyl 3-cyanoisobutyrate from prussic acid and methyl methacrylate; the second step of (b) reacting the methyl 3-cyanoisobutyrate which has been produced in the first step with water and sulfuric acid and subsequently reacting the resultant reaction product with an alcohol to produce a methylsuccinic acid ester; and the third step of (c) catalytically hydrogenating the methylsuccinic acid ester which has been produced in the second step to produce the objective 3-methyltetrahydrofuran.

The present invention also provides, as the second aspect thereof, a process for producing 3-methyltetrahydrofuran which comprises the first step of (a) producing methyl 3-cyanoisobutyrate from prussic acid and methyl methacrylate; the second step of (b') hydrating the methyl 3-cyanoisobutyrate which has been produced in the first step to produce methyl 3-carbamoylisobutyrate; the third step of (b'') producing a methylsuccinic acid ester and formamide from the methyl 3-carbamoylisobutyrate which has been produced in the second step and a formic acid ester; and the fourth step of (c) catalytically hydrogenating the methylsuccinic acid ester which has been produced in the third step to produce the objective 3-methyltetrahydrofuran.

DESCRIPTION OF PREFERRED EMBODIMENT

The process according to the first aspect of the present invention is composed of the aforesaid three steps (a), (b) and (c), while the process according to the second aspect of the present invention is composed of the aforestated four steps (a), (b'), (b") and (c).

In the first place, some description will be given of the first aspect of the present invention.

The following are the reaction formulae of the whole steps for the first aspect of the present invention.

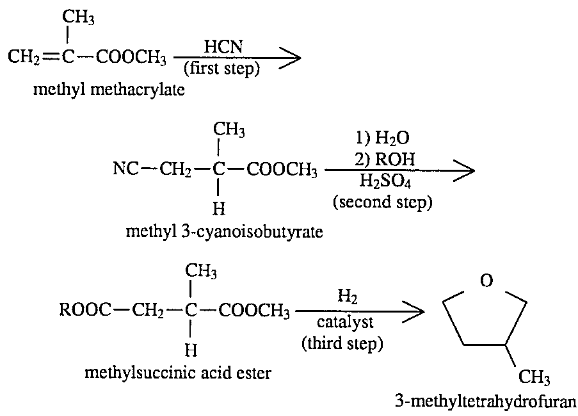

In the first step, that is, the step (a) in the first aspect of the invention, methyl 3-cyanoisobutyrate is produced from prussic acid and methyl methacrylate. The production process for the methyl 3-cyanoisobutyrate in the first step is not specifically limited, but the methyl 3-cyanoisobutyrate can be produced by a publicly known conventional process. For example, methyl 3-cyanoisobutyrate is produced by reacting prussic acid with methyl methacrylate at a temperature in the range of about 40° to 130° C. in a proper solvent such as lower alkyl-substituted pyrrolidone and dimethyl sulfoxide in the presence of a catalyst such as a cyanogen compound of an alkali metal.

In the second step, that is, the step (b), methyl 3-cyanoisobutyrate which has been prepared in the above-mentioned first step is reacted with water and sulfuric acid, and the resulting reaction product is reacted with an alcohol to produce a methylsuccinic acid ester. In more detail, water and a proper amount of sulfuric acid were added to methyl 3-cyanoisobutyrate, in which a molar amount of water is preferably 0.8 to 1.1, more preferably 0.9 to 1.05 times a molar amount of methyl 3-cyanoisobutyrate. A reaction temperature is 50° to 100° C., preferably 60° to 80° C. After the completion of the hydration reaction, the reaction product is incorporated with an alcohol in an excess amount, in a molar amount of preferably 2 to 20 times the molar amount of the methyl 3-cyanoisobutyrate to proceed with esterifying reaction at a temperature of about 70° to 160° C., preferably 100° to 140° C. with the result that the ester is formed together with acidic ammonium sulfate.

A reaction temperature higher than 160° C. in the aforesaid esterifying reaction results in the liability to increase in the by-production of an ether due to the dehydration of the alcohol, whereas that lower than 70° C. often leads to impracticality because of an unreasonably low rate of reaction.

A more preferable result is obtained when the esterifying reaction is carried out by intermittantly or continuously supplying the alcohol in a molar amount of 2 to 6 times that of methyl 3-cyanoisobutyrate so as to maintain the reaction temperature in the range of about 80° to 130° C. under the reflux of the alcohol. The alcohol to be employed in the esterifying reaction is preferably an aliphatic alcohol having 1 to 8 carbon atoms, more preferably a primary alcohol, particularly preferably methanol taking into consideration the steps of purification, separation and the like.

In the last third-step, that is, the step (c), the objective 3-methyltetrahydrofuran is produced by catalytically hydrogenating the methylsuccinic acid ester which has been prepared in the preceding second-step. The catalytically hydrogenating reaction may be of either batch system or continuous system, but is preferably of trickle bed system by the use of a fixed bed catalyst. The feed amount by weight per unit time (hour) of the methylsuccinic acid ester is about 0.05 to 1.0 times the amount by weight of the catalyst. The conditions of the catalytically hydrogenating reaction vary depending on the type of the ester as the starting material and the kind of the catalyst, but generally include a reaction temperature in the range of 100° to 300° C. and a reaction pressure of 20 k g/cm$^2$ (gauge) or higher. The hydrogen gas to be used in the above-mentioned reaction is not necessarily required to be highly pure, but may contain an inert gas such as nitrogen and methane which does not exert evil influence upon the catalytically hydrogenating reaction.

The catalyst to be used in the hydrogenating reaction in the third step preferably contain, as a principal component, copper or an element belonging to any of the groups 7a and 8 of the Periodic table. In more detail, examples of effective element as a principal component of the catalyst in the aforesaid reaction include copper, cobalt, nickel, iron, rhenium, palladium, ruthenium, platinum, and rhodium. Examples of an effective promoter include a solid acid component containing chromium, molybdenum, manganese, barium, magnesium, silicon or aluminum. As particularly preferable catalyst for the reaction, mention is made of so called copper/chromite containing copper as the principal component and the aforesaid copper/chromite incorporated with manganese, barium or the like as a promoter component.

In the case where the particularly preferable copper/chromate is used as catalyst for the hydrogenating reaction, the preferable reaction conditions include a reaction temperature of 150° to 280° C. and a reaction pressure of 50 to 200 kg/cm$^2$ G (gauge).

The particularly preferable catalyst composed of copper/chromium/barium (or manganese) is prepared, for example, in the following ways.

(1) Cupric oxide (CuO), chromium (III) oxide ($Cr_2O_3$), and manganese dioxide ($MnO_2$) or barium oxide (BaO) each in the form of solid are mixed with each other and further incorporated with graphite or the like as a lubricant with sufficient mixing, thereafter the resulting mixture is molded by a usual method and the resultant molding is calcined at a high temperature, followed by crushing into the suitable sizes for use.

(2) To the aqueous solution of ammonium dichromate which has been incorporated with aqueous ammonia is added dropwise under stirring, the aqueous solution of cupric nitrate (or cupric sulfate, etc.), and manganese nitrate (or manganese sulfate, etc.) or barium nitrate which solution has separately been prepared. The resultant precipitate is washed with water, dried and then calcined at a temperature of about 350° C., for example, in the air. The resultant calcined product in the form of powder can be used as it is for the reaction. Alternatively, it can be incorporated with an appropriate binding agent and/or a lubricant with sufficient mixing and thereafter molded for use in the form of molding.

It is preferable, in the catalyst composed of copper/chromium/barium (or manganese) which is obtained by any of the above procedures (1) and (2), that Cu:Cr:Mn or Ba ratio by weight be 20 to 85:15 to 75:1 to 15 expressed in terms of $CuO:Cr_2O_3:MnO_2$ or BaO by weight.

The catalyst may be of any form including powder and tablets, and is to be used in the form optimum for the mode of usage. Prior to use for the reaction, the catalyst is subjected to a suitable activation treatment such as a treatment at about 200° C. in an atmosphere of hydrogen.

In the catalytically hydrogenating reaction in the third step, the suitable amount of hydrogen to be used therein is at least 4 moles, preferably 6 to 60 moles per one mole of methylsuccinic acid ester. Although the reaction can be put into practice without using a solvent, it is preferable to use a solvent. There is no limitation to a solvent to be used provided that it does not exert adverse effect on the reaction and mention is made of alcohols, hydrocarbons and the like. The solvent may be used alone or in combination with at least one different solvent.

3-Methyltetrahydrofuran is formed by the aforestated catalytic hydrogenating reaction, but is accompanied with the by-production of an alcohol. Thus, the reaction liquid after the completion of the catalytically hydrogenating reaction is usually subjected to a distillation treatment to separate the 3-methyltetrahydrofuran as the objective product from the by-produced alcohol. The alcohol thus separated can be circulated, as desired, for use as a starting raw material in the second step.

Next, a description will be given of the second aspect of the present invention.

The following are the reaction formulae of the whole steps for the second aspect of the present invention.

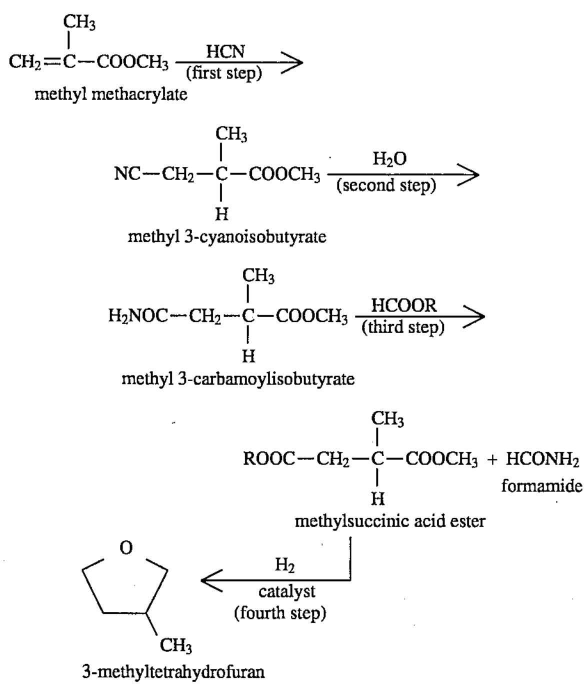

In the step (a), that is, the first step in the second aspect of the invention, methyl 3-cyanoisobutyrate is produced from prussic acid and methyl methacrylate in the same manner as in the step (a) of the first aspect of the invention.

In the second step, that is, the step (b'), methyl 3-cyanosiobutyrate which has been prepared in the aforesaid first step is hydrated to produce methyl 3-carbamoylisobutyrate. The hydrating reaction is put into practice by catalytically reacting the mixture of the methyl 3-cyanoisobutyrate and water in the presence of a catalyst. As an applicable catalyst, mention is made of a catalyst which is effective for a hydrating reaction of nitriles, including a strong acid such as sulfuric acid. Judging from the economical view point including the treatment of the used acid, a metal catalyst or a metal oxide catalyst etc. is preferable. Specific examples of effective catalysts include manganese, copper, nickel and an oxide thereof, among which manganese oxide is particularly preferable. The ratio by weight of the methyl 3-cyanoisobutyrate to water is 2:98 to 98:2 as a proper range. In this system, methyl methacrylate which is the starting raw material for methyl 3-cyanoisobutyrate, an alcohol, a ketone such as acetone or the like can be allowed to coexist as a solvent. In the case where manganese oxide is used as the catalyst, the reaction temperature is in the range of preferably 20° to 150° C., particularly preferably 30° to 100° C. The reaction time is preferably 0.3 to 6 hours, particularly preferably 0.5 to 4 hours. The reaction can be put into practice by any of a batchwise system and a continuous system. By distilling away the water and the solvent in the resultant reaction liquid through a conventional method, methyl 3-carbamoylisobutyrate is obtained.

In the third step, that is, the step (b''), the methyl 3-carbamoylisobutyrate which has been prepared in the aforesaid second step is reacted with a formic acid ester to produce a methylsuccinic acid ester and formamide. The reaction can be put into practice by heating the mixture of the methyl 3-carbamoylisobutyrate and the formic acid ester even in the absence of a catalyst, but it is effectively carried out in the presence of a solvent and a catalyst. As a formic acid ester, methyl formate is preferably used and in this case, methanol and carbon monoxide can be used in place of methyl formate. The reaction belongs to an equilibrium reaction, and the yield of the methylsuccinic acid ester depends on the molar ratio of the methyl 3-carbamoylisobutyrate to the formic acid ester. The molar ratio of the formic acid ester/methyl 3-carbamoylisobutyrate is preferably 1 to 10, particularly preferably 2 to 6. The use of a solvent is effective in increasing the solubility of methyl 3-carbamoylisobutyrate and enhancing the selectivity of the reaction. The solvent to be used is preferably the alcohol which corresponds to the ester group of the formic acid ester. The molar feed ratio of the alcohol to the methyl 3-carbamoylisobutyrate is preferably 1 to 10, particularly preferably 2 to 6. As a catalyst for the aforesaid reaction, an alcoholate of an alkali metal, an oxide of an alkaline earth metal and a strongly basic ion exchange resin are extremely excellent. The alcoholate of an alkali metal is synthesized from an alkali metal such as lithium, sodium and potassium and a lower alcohol, and is exemplified by the methylate, ethylate, butylate, etc. of any of sodium and potassium. The oxide of an alkaline earth metal is exemplified by magnesium oxide, calcium oxide and barium oxide. In the case where the alcoholate of an alkali metal, the oxide of an alkaline earth metal or the strongly basic ion exchange resin is used as the catalyst, suitable reaction conditions include a reaction temperature of 20° to 80° C., a reaction time of 0.5 to 6 hours and an amount of the catalyst to be used being 0.001 to 0.3 mole per one mole of methyl 3-carbamoylisobutyrate. The reaction product in this step can be separated and recovered by the procedure such as distillation, and unreacted materials can be returned to the starting raw material system.

Lastly, in the step (c), that is, the fourth step, the objective 3-methyltetrahydrofuran is produced by catalytically hydrogenating the methylsuccinic acid ester which has been prepared in the preceding third step, in the same manner as in the step (c) of the first aspect of the invention. The reaction liquid after the completion of the catalytically hydrogenating reaction is usually subjected to a distillation treatment to separate the 3-methyltetrahydrofuran as the objective product from the by-produced alcohol in the same manner as in the first aspect of the invention.

In the second aspect of the present invention, the formamide which is formed in the third step can be treated in the following way, as desired, and circulated for use as a starting raw material. There is available a method in which the formamide is dehydrated by a publicly known method to produce prussic acid, the resultant prussic acid is used as a starting raw material in the first step, and the dehydration reaction is put into practice at a temperature of about 350° to 600° C., usually in gas phase.

There is available another method in which the formamide is decomposed into ammonia and carbon monoxide by a publicly known method, and the decomposed products are utilized. The decomposing reaction of formamide into ammonia and carbon monoxide is carried out by heating formamide in a gas phase or a liquid phase in the absence of a catalyst or in the presence of a basic catalyst. It is preferable in the above method to carry out the decomposition at 300° C. or lower in order to suppress the by-production of prussic acid. Examples of an effective basic catalyst include activated carbon, sodium hydroxide, sodium cyanide and metal alcoholate. As a suitable example of the decomposing reaction, mention is made of that in which formamide is heated to about 120° to 220° C. in liquid phase in the presence of a catalyst under stirring, while the resultant gas mixture is taken out from the reaction system. Ammonia and carbon monoxide each being highly pure are recovered by separating ammonia from the resultant gas mixture of ammonia and carbon monoxide through cooling under pressure or absorption. The ammonia thus recovered can be made into prussic acid by an industrially publicly know process and circulated for use in the first step of the present invention. As a process for producing prussic acid from the recovered ammonia, mention is preferrably made of an ammoxidation process in which a hydrocarbon is subjected to ammoxidation by the use of ammonia and air. As the ammoxidation process, there are available the Andrussow process in the case of using methane, the Shawinnigen process in the case of using a higher alkane and the like processes. In addition, the Degussa process or the like is known as a process for producing prussic acid in the absence of oxygen. It is possible to feed the recovered ammonia to a plant for producing acrylonitrile by the ammoxidation of propylene according to the Sohio process to obtain prussic acid as the by-product. On the other hand, the carbon monoxide as such may be circulated for use through the third step together with methanol, or be reacted with methanol to carbonylate methanol into methyl formate and to circulate the resultant methyl formate for use through the third step.

The process for producing 3-methyltetrahydrofuran according to any of the first and second aspects of the present invention makes it possible to produce 3-methyltetrahydrofuran with extremely high selectivity in each of the steps in an industrially advantageous manner from inexpensive starting raw materials. The 3-methyltetrahydrofuran which is produced by the process according to the present invention is useful, for example, as a comonomer for polyether glycol to be used as a starting raw material for spandex fibers.

In the following, the present invention will be described in more detail with reference to reference examples and (working) examples, which however shall not be construed to limit the present invention thereto.

EXAMPLE 1

(1) First step (production of methyl 3-cyanoisobutyrate from prussic acid and methyl methacrylate):

A 500 milliliter (hereinafter abbreviated to "mL") flask equipped with a stirrer, a thermometer and two dropping funnels was charged with 203 g of N-methylpyrrolidone and 1.35 g of potassium cyanide, and to the content in the flask were added dropwise 40 g of prussic acid and 163 g of methyl methacrylate over a period of 4 hours, while the content was maintained at a temperature of 120° C. After the completion of the dropwise addition, the content was maintained at 120° C. for 2 hours to complete the reaction. As a result, methyl cyanoisobutyrate was formed at a conversion of methyl methacrylate (MMA) of 88.3% and at a selectivity of 98.1% based on the reacted MMA.

Subsequently the flask was connected to a reduced pressure system to recover unreacted MMA and then, 165 g of methyl 3-cyanoisobutyrate was obtained. The recovery of 3-cyanoisobutyrate inclusive of an intermediate fraction was quantitative.

(2) Second step (hydration and esterification of methyl 3-cyanoisobutyrate)

A 200 mL flask equipped with a stirrer, a thermometer and a dropping funnel was charged with 5.05 g of 97% by weight concentration of sulfuric acid and 0.81 g of water, and to the content in the flask were added dropwise 6.35 g of the methyl 3-cyanoisobutyrate which had been obtained in the preceding item (1) over a period of about 20 minutes, while the content was maintained at a temperature of 70° C. Thereafter, the content was allowed to stand at 70° C. for 2 hours to proceed with hydrolysis reaction. The resultant reaction liquid in an amount of 100 mL was transferred in a shaking type autoclave together with methanol in an amount by weight of 4 times that of the methyl 3-cyanoisobutyrate to proceed with esterification at 120° C. for 6 hours, while the pressure in the autoclave was about 7.5 kg/cm$^2$ G. Thus, dimethyl methylsuccinate was obtained at a yield of 94.2 mol % based on the fed methyl 3-cyanoisobutyrate, and the by-production of dimethyl ether was observed at 5 mol % based on the dimethyl methylsuccinate thus formed.

(3) Third step (hydrogenation of dimethyl methylsuccinate)

A catalyst available on the market under the trademark G99C produced by Nissan Girdler Co., Ltd. comprising by weight, 36% of Cuo, 32% of $Cr_2O_3$, 2.4% of $MnO_2$ and 2.2% of BaO in the form of pellet (¼ inch by ¼ inch in size) was divided into ⅛ in size, packed in a tubular reactor with 15 mm inside diameter and 300 mm length (the catalyst bed height being 97 mm) in an amount of 20.0 g, and subjected to an activating treatment by the ordinary hydrogenating reduction comprising the steps of treating the catalyst at 150° C. for 3 hours in a stream of nitrogen containing one % by volume of hydrogen; then treating the same at 180° C. overnight in a stream of nitrogen containing 2% by volume of hydrogen; then treating the same at 200° C. for 3 hours in a stream of nitrogen containing 10% by volume of hydrogen; and finally treating the same at 250° C. for 30 minutes in a stream of nitrogen containing 10% by volume of hydrogen. The catalyst thus activated was used for proceeding with a reaction under the reaction conditions including a reaction temperature of 230° C. and a reaction pressure of 160 k g/cm$^2$ G. To the reactor were fed, at the top thereof, hydrogen at a rate of 10 liters (L)/hour expressed in terms of the rate at the outlet; and 30% concentration by weight solution of the dimethyl methylsuccinate in pseudocumene (1,2,4-trimethylbenzene) which had been obtained in the preceding item (2) at a rate of 5 g/hour, that is, 0.075 hr$^{-1}$ WHSV (weight hourly space velocity; a quotient obtained when the feed rate by weight of the starting raw material is divided by the weight of the catalyst). As a result of analysis for the reaction liquid thus obtained, 3-methyltetrahydrofuran was obtained at a yield of 95.5% based on the dimethyl methylsuccinate which was fed, while unreacted dimethyl methylsuccinate was not observed.

EXAMPLE 2

The procedure in Example 1 was repeated to proceed with reaction except that in the second step of esterification, methanol in an amount by weight of 2.6 times that of the methyl 3-cyanoisobutyrate was intermittantly added dropwise to the content in the flask at 100° C. at atmospheric pressure under the reflux of methanol over a period of 5 hours; then at least 90% of water which was formed by the by-production of ether was removed outside the reaction system together with methanol; and additional methanol in an amount of 2.6 times that of the methyl 3-cyanoisobutyrate was intermittantly added dropwise to the content in the flask at 100° C. at atmospheric pressure under the reflux of methoanol over a period of 5 hours. As a result, dimethyl methylsuccinate was obtained at a yield of 97.6 mol % based on the fed methyl 3-cyanoisobutyrate, and by-production of dimethyl ether was at most 1 mol % based on the dimethyl methylsuccinate thus formed.

EXAMPLE 3

(1) First step (production of methyl 3-cyanoisobutyrate from prussic acid and MMA):

In the same manner as in Example 1 (1), methyl 3-cyanoisobutyrate was produced at a conversion of 88.3% at a selectivity of 98.1%.

(2) Second step (production of methyl 3-carbamoylisobutyrate by the hydration of methyl 3-cyanoisobutyrate)

Preparation of catalyst:

A one L flask equipped with a stirrer, a reflux cooler and a thermometer was charged with 63.2 g of potassium permanganate and 500 g of water with heating to 70° C. under stirring. To the resultant mixture were added 240 g of aqueous solution containing 59.0 g of manganese sulfate and 40 g of 15% by weight concentration of sulfuric acid to proceed with the reaction at 70° C. for 3 hours. After the content in the flask was cooled, the resulting precipitate was filtered and the precipitated cake was washed with water and dried overnight at 60° C. Thus, 74 g of activated manganese dioxide was obtained and used for the reaction described hereunder.

Hydration reaction:

A 500 mL flask equipped with a stirrer, a thermometer and a dropping funnel was charged with 80 g of the methyl cyanoisobutyrate which had been obtained in the preceding item (1), 250 g of water, 58 g of acetone and 50 g of the catalyst thus obtained to proceed with hydration reaction for 3.5 hours, while the temperature of the content in the flask was maintained at 80° C. The resultant reaction mixture was cooled and then, the catalyst was filtered away. As a result of analysis for the filtrate thus obtained, methyl 3-carbamoylisobutyrate was obtained at a conversion of 90.7% based on methyl 3-cyanoisobutyrate, and at a selectivity of 98% based on the reacted methyl 3-cyanoisobutyrate. The filtrate was concentrated under reduced pressure and recrystallized from acetone. As a result, 73 g of methyl 3-carbamoylisobutyrate having a purity of at least 99.5% was obtained.

(3) Third step (production of dimethyl methylsuccinate and formamide from methyl 3-carbamoylisobutyrate and methyl formate):

A one L stainless steel-made autoclave equipped with a stirrer was charged with 72.5 g of the methyl 3-carbamoylisobutyrate which had been obtained in the preceding item (2), 180 g of methyl formate, 96 g of methanol and 1.1 g of sodium methylate to proceed with heating reaction at 60° C. for 2 hours. The reaction product was cooled and then analyzed. As a result, the conversion of the methyl 3-carbamoylisobutyrate was 83.2% and, there were obtained dimethyl methylsuccinate at a selectivity of 99.8% based on the reacted methyl 3-carbamoylisobutyrate, and formamide at a selectivity of 98.4% based on the same. The sodium methylate in the reaction liquid was neutralized with sulfuric acid, and subsequently the reaction liquid was distilled by a conventional method. As a result, methyl formate and methanol were recovered and there were obtained 60 g of dimethyl methylsuccinate with at least 99% purity and 16 g of formamide with 99% purity. The recovery of these substances inclusive of an intermediate fraction was quantitative, respectively.

(4) Fourth step (hydrogenation of dimethyl methylsuccinate)

In the same manner as in Example 1 (3), dimethyl methylsuccinate was hydrogenated with the result that 3-methyltetrahydrofuran was obtained at a yield of 95.5% based on the fed dimethyl methylsuccinate.

REFERENCE EXAMPLE 1

(production of prussic acid by the dehydration of formamide)

Preparation of catalyst:

To 51.5 g of manganese carbonate was added a solution of 0.88 g of sodium carbonate in 30 g of water, and then the resulting mixture was kneaded for one hour. The kneaded product was dried at 110° C. for 15 hours, calcined at 450° C. for 5 hours in a stream of nitrogen containing 10% by volume of hydrogen and subsequently crushed to afford 30 g of crushed manganese oxide regulated to 10 to 20 mesh.

Reaction:

Manganese oxide in an amout of 3.0 g which had been obtained in the above-mentioned manner was packed in a quartz-made tubular reactor with 10 mm inside diameter and 300 mm length equipped with a sheath tube for thermometer to form a catalyst bed, and subsequently the catalyst was heated so as to maintain the temperature of the lower portion of the resulting catalyst bed at 400° C. Quartz-made Rasching rings of 3×3 mm in size were packed in the reactor 150 mm above the catalyst bed and heated at 100° to 400° C. to constitute the vaporizing portion of formamide. While the pressure in the reactor is maintained at a vaccum degree of 100 mmHg, formamide and air were introduced in the reactor through the top of the reactor at feed rates of 10 g/hr and 240 mL/hr, respectively. After a lapse of 5 hours from the start of the reaction, the reaction gas was sampled for one hour. The resultant prussic acid was captured and collected by absorbing it in water and aqueous solution of sodium hydroxide, and was determined by the titration with silver nitrate solution. Determinations were made of ammonia dissolved in water by ion chromatography and of unreacted formamide by gas chromatography. As a result, the conversion of the formamide was 99.5% and there were obtained prussic acid at a yield of 95.2% and ammonia at a yield of 4.3%,

REFERENCE EXAMPLE 2

(decomposition of formamide into ammonia and carbon monoxide)

A 300 mL four-necked round bottom flask equipped with a stirrer and a reflux cooler was charged with 180 g of formamide and one g of calcium oxide as a catalyst, which were heated to 150° C. by means of a mantle heater under stirring. The mist contained in the generated gas was condensed in a brine reflux cooler. The resultant ammonia gas was collected by absorbing it in aqueous solution of sulfuric acid and determined by neutralization titration. The resultant carbon monoxide was determined with a gas meter and gas chromatography. As a result, there were obtained ammonia at a yield of 94% and carbon monoxide at a yield of 89%.

EXAMPLE 4

The procedure in Example 3 (3) was repeated except that ethyl formate was used in place of methyl formate. As a result, the conversion of methyl 3-carbamoylisobutyrate was 83.7% and there were obtained methylsuccinic acid ethyl methyl ester at a selectivity of 99.8% and formamide at a selectivity of 98.6%, each based on the reacted methyl 3-carbamoylisobutyrate.

EXAMPLE 5

The procedure in Example 3 (3) was repeated to proceed with heating stirring reaction except that in place of 180 g of methyl formate and 96 g of methanol, 200 g of methanol was charged in the autoclave and carbon monoxide was pressurized into the autoclave so as to maintain the internal pressure at 40 kg/cm$^2$ G. After the temperature of the content in the autoclave reached 60° C., carbon monoxide was fed in the autoclave so as to maintain the internal pressure at 40 kg/cm$^2$ G to proceed with the reaction for 3 hours. Subsequently, the content therein was cooled, internal pressure was gradually lowered to atmospheric pressure, and the reaction product was taken out. As a result of analysis therefor, the conversion of methyl 3-carbamoylisobutyrate was 81.4% and there were obtained dimethyl methylsuccinate at a selectivity of 95.7% and formamide at a selectivity of 94.4%, each based on the reacted methyl 3-carbamoylisobutyrate.

What is claimed is:

1. A process for producing 3-methyltetrahydrofuran which comprises:

(a) producing methyl 3-cyanoisobutyrate from prussic acid and methyl methacrylate;

(b) reacting the methyl 3-cyanoisobutyrate from step (a) with water and sulfuric acid and subsequently reacting the resultant reaction product with an aliphatic alcohol having 1 to 8 carbon atoms to produce a methylsuccinic acid ester; and (c) catalytically hydrogenating the methylsuccinic acid ester from step (b) to produce the 3-methyltetrahydrofuran.

2. The process according to claim 1, wherein the alcohol having 1 to 8 carbon atoms is intermittently or continuously supplied in a molar amount of 2 to 6 times that of the methyl 3-cyanoisobutyrate to proceed with an esterifying reaction in step (b).

3. The process according to claim 1, wherein the alcohol having 1 to 8 carbon atoms in step (b) is methanol.

4. A process for producing 3-methyltetrahydrofuran which comprises (a) producing methyl 3-cyanoisobutyrate from prussic acid and methyl methacrylate;

(b') hydrating the methyl 3-cyanoisobutyrate from step (a) to produce methyl 3-carbamoylisobutyrate;

(b") reacting the methyl 3-carbamoylisobutyrate from step (b') with a formic acid ester or with methanol and carbon monoxide to produce a methylsuccinic acid ester and formamide; and (c) catalytically hydrogenating the methylsuccinic acid ester from step (b") to produce the 3-methyltetrahydrofuran.

5. The process according to claim 4, wherein step (b") is carried out with a formic acid ester which is methyl formate.

6. The process according to claim 5, wherein step (b") is carried out with methanol and carbon monoxide.

7. The process according to claim 4, wherein the prussic acid in step (a) is produced by dehydrating the formamide which is formed in the third step.

8. The process according to claim 4, wherein the prussic acid in step (a) is produced by decomposing the formamide which is formed in step (b") into a mixed gas of ammonia and carbon monoxide and subjecting a hydrocarbon to ammoxidation in the presence of air and said ammonia which is recovered from said mixed gas.

9. The process according to claim 5, wherein the methyl formate in step (b") is produced by decomposing the formamide which is formed in step (b") into a mixed gas of ammonia and carbon monoxide and carbonylating methanol by said carbon monoxide which is recovered from said mixed gas.

10. The process according to claim 5, wherein step (b") is carried out with methanol and carbon monoxide which is produced by decomposing the formamide that is formed in step (b") into a mixed gas of ammonia and carbon monoxide.

11. The process according to claim 1, wherein step (a) is carried out at a temperature of 40° to 130° C. in the presence of a solvent selected from the group consisting of a lower alkyl-substituted pyrrolidone and dimethyl sulfoxide and in the presence of a catalyst which is a cyanogen compound of an alkali metal; the reaction with water and sulfuric acid in step (b) is carried out at a temperature of 50° to 100° C. with 0.8 to 1.1 moles of water per mole of the methyl 3-cyanoisobutyrate; in step (b), the alcohol is in an amount of 2 to 20 times the molar amount of the methyl 3-cyanoisobutyrate and the reaction with the aliphatic alcohol is carried out at a temperature of 70° to 160° C.; and step (c) is carried out with a feed amount by weight per hour of the methylsuccinic acid being 0.05 to 1.0 times the amount by weight of a catalyst, at a temperature of 100° C. to 300° C. and a pressure of 20 kg/cm$^2$G or higher.

12. The process according to claim 11, wherein the reaction with water and sulfuric acid in step (b) is carried out at a temperature of 60° C. to 80° C.; the reaction with alcohol in step (b) is carried out at a temperature of 100° to 140° C.; and step (c) is carried out with a copper/chromate catalyst at a temperature of 150° C. to 280° C. and at a pressure of 50 to 200 kg/cm$^2$G.

13. The process according to claim 12, wherein step (c) is carried out with 6 to 60 moles of hydrogen per mole of the methylsuccinic acid ester.

14. The process according to claim 5, wherein step (a) is carried out at a temperature of 40° to 130° C. in the presence of a solvent selected from the group consisting of a lower alkyl-substituted pyrrolidone and in the presence of a catalyst which is a cyanogen compound; step (b') is carried out in the presence of a catalyst which is manganese oxide with a weight ratio of the methyl 3-cyanoisobutyrate to water of 2:98 to 98:2, at a temperature of 20° to 150° C. and for a reaction time of 0.3 to 6 hours; step (b") is carried out with a molar ratio of the formic acid ester to the methyl 3-carbamoylisobutyrate of 1 to 10; and step (c) is carried out with a feed amount by weight per hour of the methylsuccinic acid being 0.05 to 1.0 times the amount by weight of a catalyst, at a temperature of 100° C. to 300° C. and a pressure of 20 $kg/cm^2G$ or higher.

15. The process according to claim 14, wherein step (b') is carried out at a temperature of 30° to 100° C. for a reaction time of 0.5 to 4 hours; and step (b") is carried out with a molar ratio of the formic acid ester to the methyl 3-carbamoylisobutyrate of 2 to 6.

* * * * *